US009757164B2

(12) United States Patent
Hess et al.

(10) Patent No.: US 9,757,164 B2
(45) Date of Patent: Sep. 12, 2017

(54) INTERSPINOUS PROCESS IMPLANT HAVING DEPLOYABLE ANCHOR BLADES

(71) Applicant: Spinal Simplicity LLC, Lenexa, KS (US)

(72) Inventors: Harold Hess, Leawood, KS (US); Adam Frock, Larwell, IN (US); Melissa Frock, Larwill, IN (US); Todd Moseley, Olathe, KS (US); Adam Rogers, Norfolk, VA (US); Jonathan Hess, Kansas City, MO (US)

(73) Assignee: Spinal Simplicity LLC, Lenexa, KS (US)

( * ) Notice: Subject to any disclaimer, the term of this patent is extended or adjusted under 35 U.S.C. 154(b) by 817 days.

(21) Appl. No.: 13/940,868

(22) Filed: Jul. 12, 2013

(65) Prior Publication Data
US 2014/0194930 A1 Jul. 10, 2014

Related U.S. Application Data

(60) Provisional application No. 61/749,595, filed on Jan. 7, 2013.

(51) Int. Cl.
*A61B 17/70* (2006.01)
(52) U.S. Cl.
CPC ................. *A61B 17/7065* (2013.01)
(58) Field of Classification Search
CPC ............ A61B 17/7065; A61B 17/7067; A61B 17/7068
See application file for complete search history.

(56) References Cited

U.S. PATENT DOCUMENTS

| 1,346,578 | A | 7/1920 | Windsor |
| 4,116,104 | A | 9/1978 | Kennedy |

(Continued)

FOREIGN PATENT DOCUMENTS

| CN | 102137628 A | 7/2011 |
| GB | 2 436 292 A | 9/2007 |

(Continued)

OTHER PUBLICATIONS

US 7,520,878, 04/2009, Michelson (withdrawn)

(Continued)

*Primary Examiner* — Jan Christopher Merene
*Assistant Examiner* — Atiya Mahmud
(74) *Attorney, Agent, or Firm* — Locke Lord LLP; Scott D. Wofsy; Arpita G. Buesing

(57) ABSTRACT

An interspinous process implant is disclosed that includes a body defining a longitudinal axis, an interior cavity and opposed proximal and distal end portions, a pair of anchor wings operatively associated with the distal end portion of the body and mounted for pivotal movement relative to the longitudinal axis of the body between a first position housed within the interior cavity of the body and a second position extending radially outwardly from the body, an anchor collar operatively associated with the proximal portion of the body and mounted for axial movement relative to the longitudinal axis of the body between a first position spaced apart from the anchor wings and a second position approximated with the anchor wings, a pair of anchor blades operatively associated with the anchor collar and mounted for movement between a first position housed at least partially within the interior cavity of the body and a second position extending radially outwardly from the anchor collar.

19 Claims, 12 Drawing Sheets

(56) References Cited

U.S. PATENT DOCUMENTS

| | | | |
|---|---|---|---|
| 4,573,844 A | 3/1986 | Smith | |
| 4,599,086 A | 7/1986 | Doty | |
| 4,632,101 A | 12/1986 | Freedland | |
| 4,721,103 A | 1/1988 | Freedland | |
| 4,998,936 A | 3/1991 | Mehdian et al. | |
| 5,098,433 A | 3/1992 | Freedland | |
| 5,209,621 A | 5/1993 | Burbidge | |
| 5,417,531 A | 5/1995 | Brown | |
| 5,499,894 A | 3/1996 | Alto et al. | |
| 5,514,180 A | 5/1996 | Heggeness et al. | |
| 5,609,635 A * | 3/1997 | Michelson | A61F 2/30744 606/247 |
| 5,645,599 A | 7/1997 | Samani | |
| 5,653,761 A | 8/1997 | Pisharodi | |
| 5,702,391 A | 12/1997 | Lin | |
| 5,800,547 A | 9/1998 | Schafer et al. | |
| 5,800,550 A | 9/1998 | Sertich | |
| 5,836,948 A | 11/1998 | Zucherman et al. | |
| 5,849,004 A | 12/1998 | Bramlet | |
| 5,860,977 A | 1/1999 | Zucherman et al. | |
| 5,876,404 A | 3/1999 | Zucherman et al. | |
| 5,876,457 A | 3/1999 | Picha et al. | |
| 5,894,004 A | 4/1999 | Wagner et al. | |
| 5,904,686 A | 5/1999 | Zucherman et al. | |
| 5,968,098 A | 10/1999 | Winslow | |
| 6,017,342 A | 1/2000 | Rinner | |
| 6,045,552 A | 4/2000 | Zucherman et al. | |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,090,112 A | 7/2000 | Zucherman et al. | |
| 6,093,207 A | 7/2000 | Pisharodi | |
| 6,149,652 A | 11/2000 | Zucherman et al. | |
| 6,152,926 A | 11/2000 | Zucherman et al. | |
| 6,156,038 A | 12/2000 | Zucherman et al. | |
| 6,174,334 B1 | 1/2001 | Suddaby | |
| 6,183,471 B1 | 2/2001 | Zucherman et al. | |
| 6,190,387 B1 | 2/2001 | Zucherman et al. | |
| 6,203,260 B1 | 3/2001 | Henline et al. | |
| 6,235,030 B1 | 5/2001 | Zucherman et al. | |
| 6,238,397 B1 | 5/2001 | Zucherman et al. | |
| 6,245,108 B1 | 6/2001 | Biscup | |
| 6,257,803 B1 * | 7/2001 | McCabe | E02D 3/12 405/269 |
| 6,264,677 B1 | 7/2001 | Simon et al. | |
| 6,280,444 B1 | 8/2001 | Zucherman et al. | |
| 6,332,882 B1 | 12/2001 | Zucherman et al. | |
| 6,332,883 B1 | 12/2001 | Zucherman et al. | |
| 6,379,355 B1 | 4/2002 | Zucherman et al. | |
| 6,402,750 B1 | 6/2002 | Atkinson et al. | |
| 6,419,676 B1 | 7/2002 | Zucherman et al. | |
| 6,419,677 B2 | 7/2002 | Zucherman et al. | |
| 6,451,019 B1 | 9/2002 | Zucherman et al. | |
| 6,451,020 B1 | 9/2002 | Zucherman et al. | |
| 6,478,796 B2 | 11/2002 | Zucherman et al. | |
| 6,500,178 B2 | 12/2002 | Zucherman et al. | |
| 6,514,256 B2 | 2/2003 | Zucherman et al. | |
| 6,610,092 B2 | 8/2003 | Ralph et al. | |
| 6,626,944 B1 | 9/2003 | Taylor | |
| 6,652,527 B2 | 11/2003 | Zucherman et al. | |
| 6,652,534 B2 | 11/2003 | Zucherman et al. | |
| 6,682,564 B1 | 1/2004 | Duarte | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,709,435 B2 | 3/2004 | Lin | |
| 6,712,819 B2 | 3/2004 | Zucherman et al. | |
| 6,733,534 B2 | 5/2004 | Sherman | |
| 6,743,256 B2 | 6/2004 | Mason | |
| 6,746,485 B1 | 6/2004 | Zucherman et al. | |
| 6,761,720 B2 | 7/2004 | Senegas | |
| 6,770,096 B2 | 8/2004 | Bolger et al. | |
| 6,783,546 B2 | 8/2004 | Zucherman et al. | |
| 6,796,983 B1 | 9/2004 | Zucherman et al. | |
| 6,849,093 B2 | 2/2005 | Michelson | |
| 6,860,977 B2 | 3/2005 | Heinz et al. | |
| 6,884,012 B2 | 4/2005 | Panasik | |
| 6,902,566 B2 | 6/2005 | Zucherman et al. | |
| 6,926,728 B2 | 8/2005 | Zucherman et al. | |
| 6,946,000 B2 | 9/2005 | Senegas et al. | |
| 6,949,123 B2 | 9/2005 | Reiley | |
| 7,001,126 B2 | 2/2006 | Lesecq | |
| 7,029,473 B2 | 4/2006 | Zucherman et al. | |
| 7,041,135 B2 | 5/2006 | Michelson | |
| 7,083,649 B2 | 8/2006 | Zucherman et al. | |
| 7,101,375 B2 | 9/2006 | Zucherman et al. | |
| 7,125,425 B2 | 10/2006 | Foley et al. | |
| 7,189,234 B2 | 3/2007 | Zucherman et al. | |
| 7,192,446 B2 | 3/2007 | Shapiro et al. | |
| 7,201,751 B2 | 4/2007 | Zucherman et al. | |
| 7,217,291 B2 | 5/2007 | Zucherman et al. | |
| 7,226,261 B1 | 6/2007 | Bristol | |
| 7,232,464 B2 | 6/2007 | Mathieu et al. | |
| 7,238,186 B2 | 7/2007 | Zdeblick et al. | |
| 7,238,204 B2 | 7/2007 | Le Couedic et al. | |
| 7,241,094 B1 | 7/2007 | Potts et al. | |
| 7,306,628 B2 | 12/2007 | Zucherman et al. | |
| 7,320,707 B2 | 1/2008 | Zucherman et al. | |
| 7,326,248 B2 | 2/2008 | Michelson | |
| 7,410,501 B2 | 8/2008 | Michelson | |
| 7,423,268 B2 | 9/2008 | Ren | |
| 7,445,636 B2 | 11/2008 | Michelson | |
| 7,445,637 B2 | 11/2008 | Taylor | |
| 7,465,317 B2 | 12/2008 | Malberg et al. | |
| 7,465,318 B2 | 12/2008 | Sennett et al. | |
| 7,476,251 B2 | 1/2009 | Zucherman et al. | |
| 7,481,839 B2 | 1/2009 | Zucherman et al. | |
| 7,481,840 B2 | 1/2009 | Zucherman et al. | |
| 7,497,859 B2 | 3/2009 | Zucherman et al. | |
| 7,503,935 B2 | 3/2009 | Zucherman et al. | |
| 7,510,567 B2 | 3/2009 | Zucherman et al. | |
| 7,520,899 B2 | 4/2009 | Zucherman et al. | |
| 7,662,187 B2 | 2/2010 | Zucherman et al. | |
| 7,824,429 B2 | 11/2010 | Culbert et al. | |
| 7,918,875 B2 | 4/2011 | Lins et al. | |
| 8,007,517 B2 | 8/2011 | Lins et al. | |
| 8,132,435 B2 | 3/2012 | Thomas et al. | |
| 8,157,840 B2 | 4/2012 | Zucherman et al. | |
| 8,343,190 B1 | 1/2013 | Mueller et al. | |
| 8,403,959 B2 * | 3/2013 | Dollinger | A61B 17/7065 606/248 |
| D692,562 S | 10/2013 | Hess | |
| 8,702,757 B2 * | 4/2014 | Thommen | A61B 17/7065 606/249 |
| 8,858,598 B2 | 10/2014 | Seifert et al. | |
| 8,945,184 B2 | 2/2015 | Hess et al. | |
| 9,314,276 B2 | 4/2016 | Hess et al. | |
| 2001/0046429 A1 | 11/2001 | Gaudron | |
| 2002/0015629 A1 | 2/2002 | Ito | |
| 2002/0100244 A1 | 8/2002 | Carroll | |
| 2004/0024463 A1 | 2/2004 | Thomas et al. | |
| 2004/0127906 A1 | 7/2004 | Culbert et al. | |
| 2004/0193158 A1 | 9/2004 | Lim et al. | |
| 2004/0208722 A1 | 10/2004 | Kuenzel | |
| 2005/0049590 A1 * | 3/2005 | Alleyne | A61F 2/442 623/17.11 |
| 2005/0053444 A1 | 3/2005 | Panasik | |
| 2005/0080425 A1 | 4/2005 | Bhatnagar et al. | |
| 2005/0129482 A1 | 6/2005 | Wang | |
| 2005/0165398 A1 | 7/2005 | Reiley | |
| 2005/0196420 A1 | 9/2005 | Zucherman et al. | |
| 2005/0245929 A1 | 11/2005 | Winslow et al. | |
| 2006/0036258 A1 | 2/2006 | Zucherman et al. | |
| 2006/0064165 A1 | 3/2006 | Zucherman et al. | |
| 2006/0064166 A1 | 3/2006 | Zucherman et al. | |
| 2006/0084985 A1 | 4/2006 | Kim | |
| 2006/0089718 A1 | 4/2006 | Zucherman et al. | |
| 2006/0095136 A1 | 5/2006 | McLuen | |
| 2006/0100710 A1 | 5/2006 | Gutlin et al. | |
| 2006/0182514 A1 | 8/2006 | Ito | |
| 2006/0184247 A1 | 8/2006 | Edidin et al. | |
| 2006/0195102 A1 | 8/2006 | Malandain | |
| 2006/0241621 A1 | 10/2006 | Moskowitz et al. | |
| 2006/0241770 A1 | 10/2006 | Rhoda et al. | |

(56) References Cited

U.S. PATENT DOCUMENTS

| | | | |
|---|---|---|---|
| 2006/0247634 A1 | 11/2006 | Warner et al. | |
| 2006/0247783 A1 | 11/2006 | McKay | |
| 2006/0264938 A1 | 11/2006 | Zucherman et al. | |
| 2006/0264939 A1 | 11/2006 | Zucherman et al. | |
| 2006/0265066 A1 | 11/2006 | Zucherman et al. | |
| 2006/0265067 A1 | 11/2006 | Zucherman et al. | |
| 2006/0271049 A1 | 11/2006 | Zucherman et al. | |
| 2006/0271194 A1 | 11/2006 | Zucherman et al. | |
| 2007/0010813 A1 | 1/2007 | Zucherman et al. | |
| 2007/0032790 A1 | 2/2007 | Aschmann et al. | |
| 2007/0055291 A1 | 3/2007 | Birkmeyer et al. | |
| 2007/0093830 A1 | 4/2007 | Zucherman et al. | |
| 2007/0185490 A1 | 8/2007 | Implicito | |
| 2007/0225706 A1 | 9/2007 | Clark et al. | |
| 2007/0270840 A1 | 11/2007 | Chin et al. | |
| 2008/0027438 A1 | 1/2008 | Abdou | |
| 2008/0071378 A1 | 3/2008 | Zucherman et al. | |
| 2008/0108990 A1 | 5/2008 | Mitchell et al. | |
| 2008/0132949 A1 | 6/2008 | Aferzon et al. | |
| 2008/0147190 A1 | 6/2008 | Dewey et al. | |
| 2008/0147193 A1 | 6/2008 | Matthis et al. | |
| 2008/0177306 A1 | 7/2008 | Lamborne et al. | |
| 2008/0183211 A1 | 7/2008 | Lamborne et al. | |
| 2008/0243250 A1 | 10/2008 | Seifert et al. | |
| 2008/0243254 A1 | 10/2008 | Butler | |
| 2008/0253860 A1 | 10/2008 | McDuff et al. | |
| 2008/0281359 A1 | 11/2008 | Abdou | |
| 2008/0312741 A1 | 12/2008 | Lee et al. | |
| 2008/0319481 A1 | 12/2008 | Moore | |
| 2009/0054988 A1 | 2/2009 | Hess | |
| 2009/0164020 A1 | 6/2009 | Janowski et al. | |
| 2009/0198338 A1 | 8/2009 | Phan | |
| 2009/0234389 A1 | 9/2009 | Chuang et al. | |
| 2009/0254185 A1 | 10/2009 | Dollinger | |
| 2009/0265006 A1 | 10/2009 | Seifert et al. | |
| 2009/0281626 A1 | 11/2009 | Farr | |
| 2009/0292316 A1* | 11/2009 | Hess | A61B 17/7065 606/249 |
| 2010/0057130 A1 | 3/2010 | Yue | |
| 2010/0106190 A1 | 4/2010 | Linares | |
| 2010/0106191 A1 | 4/2010 | Yue et al. | |
| 2010/0114166 A1 | 5/2010 | Kohm et al. | |
| 2010/0152775 A1 | 6/2010 | Seifert et al. | |
| 2010/0179655 A1 | 7/2010 | Hansell et al. | |
| 2010/0234889 A1 | 9/2010 | Hess | |
| 2010/0318127 A1* | 12/2010 | Phan | A61B 17/7065 606/249 |
| 2011/0066186 A1* | 3/2011 | Boyer, II | A61B 17/7065 606/249 |
| 2011/0160773 A1* | 6/2011 | Aschmann | A61B 17/7065 606/249 |
| 2011/0190817 A1 | 8/2011 | Thommen et al. | |
| 2011/0270257 A1 | 11/2011 | Moore | |
| 2012/0109203 A1 | 5/2012 | Dryer et al. | |
| 2012/0109205 A1 | 5/2012 | Mitchell et al. | |
| 2012/0150228 A1* | 6/2012 | Zappacosta | A61B 17/7068 606/248 |
| 2014/0194930 A1 | 7/2014 | Hess et al. | |
| 2014/0371797 A1 | 12/2014 | Seifert et al. | |
| 2015/0112387 A1 | 4/2015 | Hess et al. | |

FOREIGN PATENT DOCUMENTS

| | | | |
|---|---|---|---|
| TW | 200927063 A | | 7/2009 |
| WO | 2008/088613 A2 | | 7/2008 |
| WO | 2008/118907 A2 | | 10/2008 |
| WO | 2009/132059 A1 | | 10/2009 |
| WO | WO2011141869 | * | 11/2011 |

OTHER PUBLICATIONS

Medtronic: CD Horizon Spire (Trademark), Stabilization System, Information Brochure, James Robinson, MD, 2006.

St. Francis Medical Technologies, Inc., "A Patient's Guide to Lumbar Spinal Stenosis," & " X Stop (Trademark)—Interspinous. Process Decompression," Information Guide, Sep. 16, 2005.

International Search Report and Written Opinion of the International Searching Authority for International Application No. PCT/US2014/0101457, mailed Jun. 16, 2014.

International Search Report in PCT/US08/01231 dated Aug. 29, 2008.

Written Opinion in PCT/US08/01231 dated Aug. 29, 2008.

International Search Report in PCT/US09/006742 dated Apr. 16, 2010.

Written Opinion in PCT/US09/006742 dated Apr. 16, 2010.

Extended Search Report issued Jun. 17, 2016 in connection with EP14735285.0.

International Search Report and Written Opinion for International Application No. PCT/US2016/033277, dated Sep. 14, 2016.

First Office Action for Chinese Patent Application No. 201480012125.4, dated Jan. 12, 2017.

* cited by examiner

INTERSPINOUS PROCESS IMPLANT HAVING DEPLOYABLE ANCHOR BLADES

CROSS-REFERENCE TO RELATED APPLICATIONS

This application claims the benefit of priority to U.S. Provisional Patent Application Ser. No. 61/749,595, filed Jan. 7, 2013, which application is incorporated herein by reference in its entirety.

BACKGROUND OF THE INVENTION

1. Field of the Invention

The subject invention is directed to surgical implants, and more particularly, to a percutaneous interspinous process implant and fusion device.

2. Description of Related Art

The spine consists of a column of twenty-four vertebrae that extend from the skull to the hips. Discs of soft tissue are disposed between adjacent vertebrae. In addition, the spine encloses and protects the spinal cord, defining a bony channel around the spinal cord, called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord or nerve roots. This condition is called spinal stenosis, which results in pain and numbness in the back and legs, weakness and/or a loss of balance. These symptoms often increase after walking or standing for a period of time.

There are number of non-surgical treatments for spinal stenosis. These include non-steroidal anti-inflammatory drugs to reduce the swelling and pain, and corticosteroid injections to reduce swelling and treat acute pain. While some patients may experience relief from symptoms of spinal stenosis with such treatments, many do not, and thus turn to surgical treatment. The most common surgical procedure for treating spinal stenosis is decompressive laminectomy, which involves removal of parts of the vertebrae. The goal of the procedure is to relieve pressure on the spinal cord and nerves by increasing the area of the spinal canal.

Interspinous process decompression (IPD) is a less invasive surgical procedure for treating spinal stenosis. With IPD surgery, there is no removal of bone or soft tissue. Instead, an implant or spacer device is positioned behind the spinal cord or nerves between the interspinous processes that protrude from the vertebrae in the lower back. A well-known implant used for performing IPD surgery is described in U.S. Pat. No. 6,419,676, the disclosure of which is herein incorporated by reference in its entirety. However, implantation and deployment of this prior art device still requires an incision to access the spinal column.

An interspinous process implant placed in a minimally invasive surgical procedure is disclosed in U.S. Patent Application Publication 2008/0243250, which is also incorporated herein by reference in its entirety. This implant functions as a spacer between two adjacent spinous processes, but it is not designed to stabilize the spinous process and can migrate over time.

It would be advantageous to provide an implant for performing IPD procedures that can be percutaneously inserted into the interspinous process space to effectively treat lumbar spinal stenosis by distracting, or maintaining distraction, and sufficiently stabilizing adjacent spinous processes, and thus, adjacent vertebrae. The interspinous process implant of the subject invention, achieves those objectives.

SUMMARY OF THE INVENTION

The subject invention is directed to a new and useful interspinous process implant, which includes an elongated body dimensioned and configured for percutaneous interspinous process implantation. The body has a longitudinal axis, an interior cavity and opposed proximal and distal end portions. A pair of anchor wings is operatively associated with the distal end portion of the body and they are mounted for pivotal movement relative to the longitudinal axis of the body between a first position housed within the interior cavity of the body and a second position extending radially outwardly from the body.

An anchor collar is operatively associated with the proximal end portion of the body and is mounted for axial movement relative to the longitudinal axis of the body between a first position spaced apart from the anchor wings and a second position approximated with the anchor wings. A pair of anchor blades is operatively associated with the anchor collar and they are mounted for movement between a first position housed at least partially within the interior cavity of the body and a second position extending radially outwardly from the anchor collar.

An elongated actuation shaft is mounted for axial movement within the interior cavity of the body and it has a distal actuation portion for moving the anchor wings from their first position to their second position and a proximal actuation portion for moving the anchor blades from their first position to their second position. In addition, means are provided for moving the actuation shaft within the interior cavity of the body.

In one embodiment of the subject invention, the anchor blades are mounted for pivotal movement on the anchor collar between their first and second positions. In another embodiment of the subject invention, the anchor blades are mounted for sliding movement on the anchor collar between their first and second positions.

Preferably, each anchor wing has a proximally facing engagement surface having a plurality of spikes provided thereon for engaging the spinous process. Also, each anchor blade preferably has a distally facing engagement surface having a plurality of spikes provided thereon for engaging the spinous process.

The anchor wings are diametrically opposed to one another relative to the longitudinal axis of the body and the anchor blades are diametrically opposed to one another relative to the longitudinal axis of the body. Preferably, the diametrically opposed anchor wings are axially aligned with the diametrically opposed anchor blades.

The implant further includes a locking ring for securing the axial position of the anchor collar with respect to the elongated body. The locking ring has a pair of diametrically opposed, arcuate shaped, cantilevered pawls, each with distal facing teeth for engaging a corresponding set of teeth on the proximal facing surface of the anchor collar. The locking ring has a hexagonal nut portion on its proximal-most surface for interaction with a surgical hand tool.

These and other features of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the subject invention without undue experimentation, preferred embodiments thereof will be described in detail hereinbelow with reference to certain figures, wherein.

DETAILED DESCRIPTION OF PREFERRED EMBODIMENTS

Figure 1:
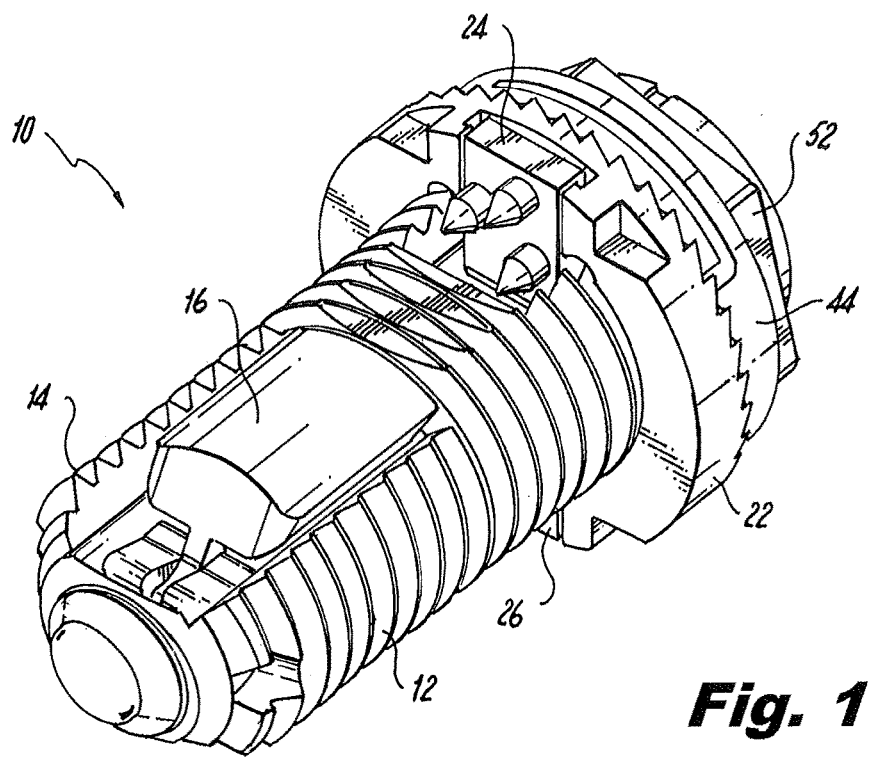
FIG. 1 is a perspective view of an interspinous process implant constructed in accordance with a preferred embodiment of the subject invention with the distal anchor wings and slidably cammed proximal anchor blades in their stowed positions.

Referring now to the drawings wherein like reference numerals identify similar structural features or aspects of the surgical implants disclosed herein, there is illustrated in FIG. 1 a preferred embodiment of an interspinous process implant constructed in accordance with a preferred embodiment of the subject invention and designated generally by reference numeral 10.

Figure 2:
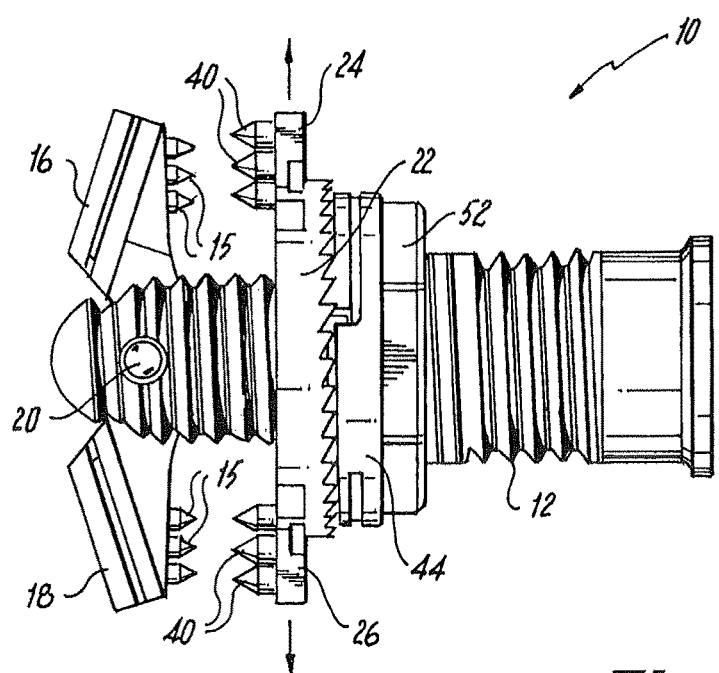
FIG. 2 is a side elevational view of the interspinous process implant of FIG. 1, wherein the distal anchor wings are shown in a radially deployed position and the slidably cammed proximal anchor blades are shown in a radially deployed position, approximated with the distal anchor wings.
Figure 3:
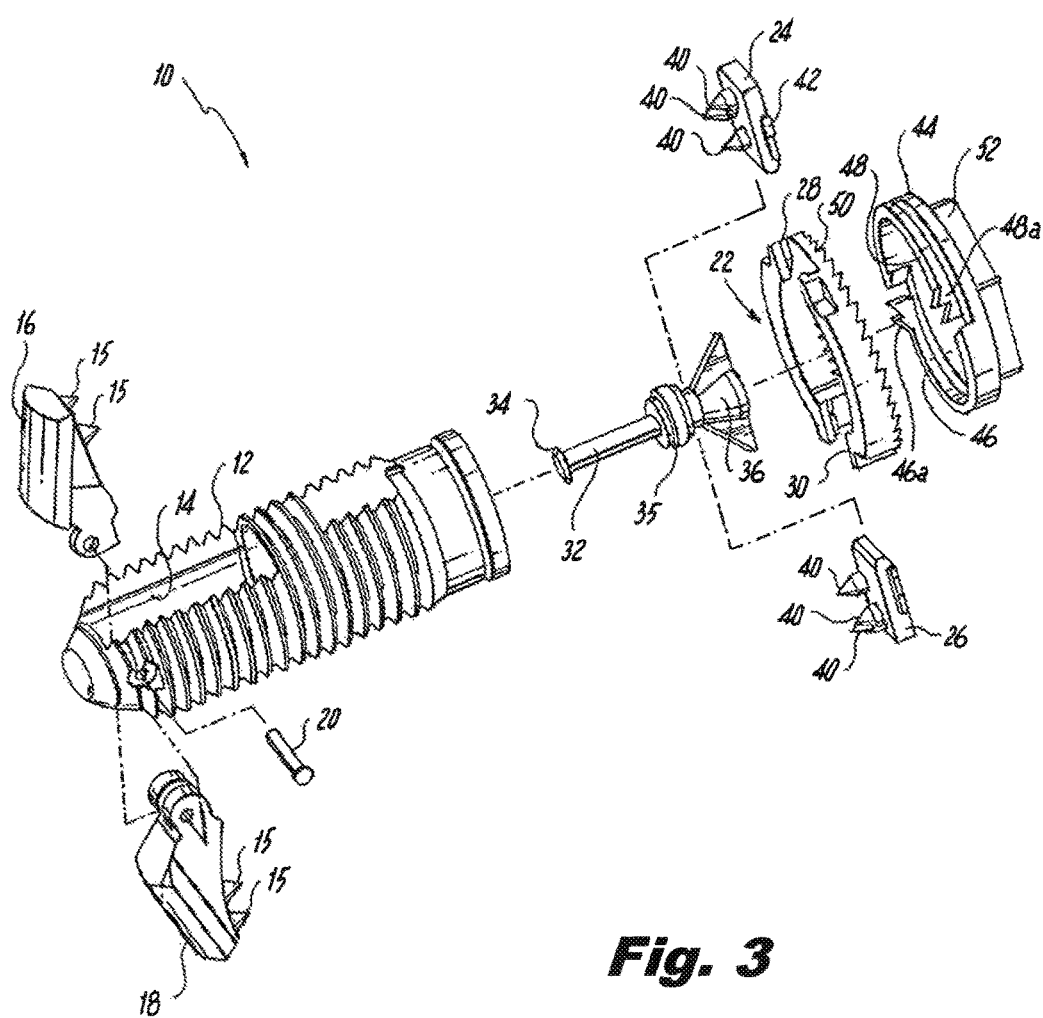
FIG. 3 is an exploded perspective view of the interspinous process implant of FIG. 1, with parts separate for ease of illustration.

Referring to FIGS. 1-3, implant 10 includes an elongated threaded body 12 which is dimensioned and configured for percutaneous interspinous process implantation by a physician. The threaded body 12 has a longitudinal axis, an interior cavity 14 and opposed proximal and distal end portions. Here and throughout the specification distal refers to the forward end of the device and proximal refers to the rearward end of the device.

A pair of anchor wings 16, 18 are operatively associated with the distal end portion of the body 12 and are mounted for pivotal movement about a pin 20 extending perpendicular to the longitudinal axis of the body 12, between a first position housed within the interior cavity of the body 12, as shown in FIG. 1 and a second position extending radially outwardly from the body 12, as shown in FIG. 2. Each anchor wing 16, 18 has a proximally facing engagement surface having a plurality of spikes 15 provided thereon for positively engaging the spinous process.

An anchor collar 22 is operatively associated with the proximal end portion of the body 12 and is mounted for axial movement relative to the longitudinal axis of the body 12 between a first position spaced apart from the anchor wings 16, 18, as shown in FIG. 1, and a second position approximated with the anchor wings 16, 18, as shown in FIG. 2. A pair of anchor blades 24, 26 is operatively associated with the anchor collar 22 and they are mounted for movement between a first position housed at least partially within the interior cavity 14 of the body 12, as shown in FIG. 1, and a second position extending radially outwardly from the anchor collar 22, as shown in FIG. 2. The anchor blades 24, 26 reside within diametrically opposed channels 28, 30 formed in the anchor collar 22, as best seen in FIG. 3.

An elongated actuation shaft 32 is mounted for axial movement within the interior cavity 14 of the body 12 and it has a distal actuation portion or plunger 34 for moving the anchor wings 16, 18 from their first position to their second position. More particularly, the plunger shaped distal actuation portion 34 urges against the inner abutment surfaces of the anchor wings 16, 18 to forcibly pivot them to a deployed position. This interaction is described in more detail in U.S. Pub. No. 2010/0234889, which is herein incorporated by reference in its entirety.

The actuation shaft 32 further includes a central hub portion 35 with an annular grommet for maintaining the axial position of the shaft 32 within the body 12, a proximal actuation portion 36 for moving the anchor blades 24, 26 from their first position to their second position. In addition, structure is provided for moving the actuation shaft 32 within the interior cavity 14 of the body 12, such as, for example, the deployment tool or insertion device disclosed in U.S. Pub. No. 2010/0234889, or an equivalent thereof.

Figure 4:
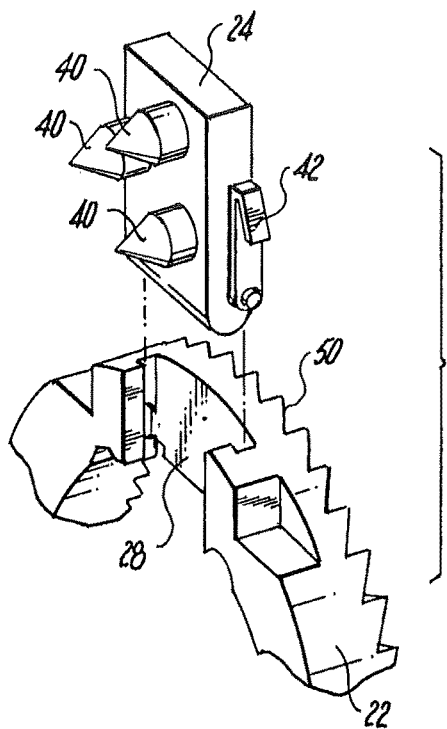
FIG. 4 is a localized perspective view of the anchor collar of the interspinous process implant of FIG. 1, with a proximal anchor blade separated therefrom for ease of illustration and showing the deflectable locking tab associated therewith.
Figure 5:
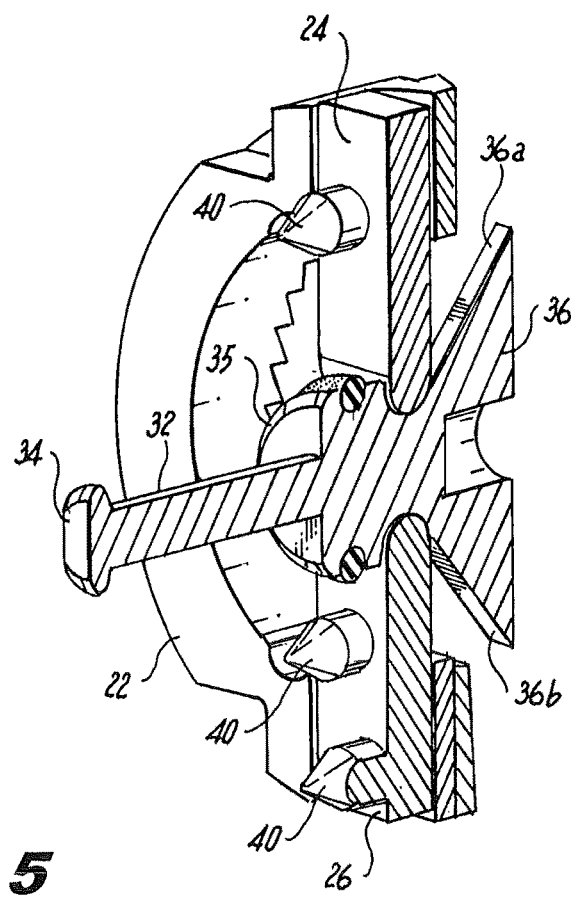
FIG. 5 is a perspective view of the anchor collar and proximal anchor blades in cross-section, together with the actuation shaft that is adapted and configured to move the proximal anchor blades and distal anchor wings from their stowed positions to their deployed positions.
Figure 6:
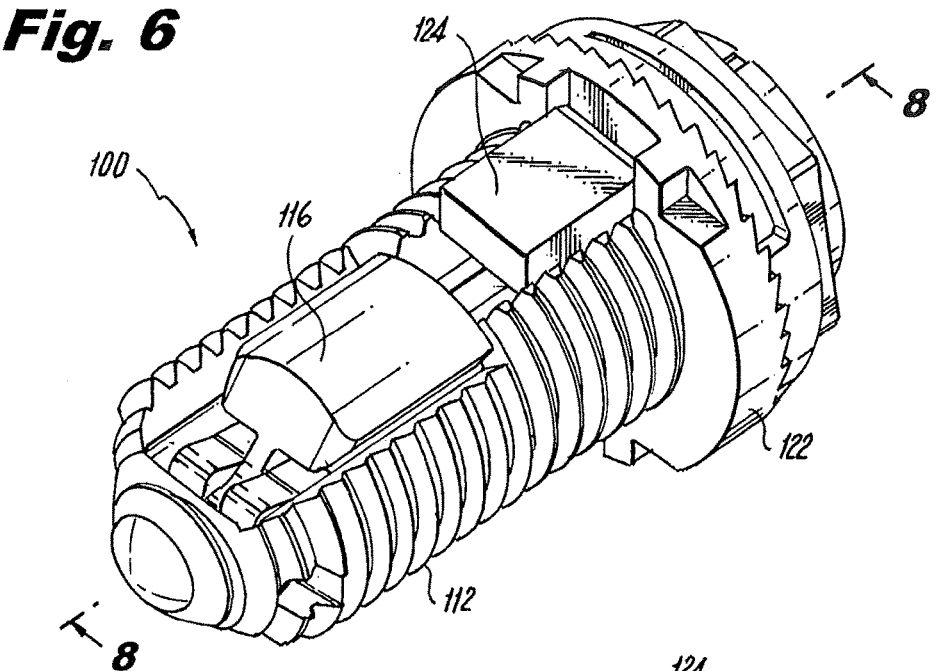
FIG. 6 is a perspective view of another interspinous process implant constructed in accordance with a preferred embodiment of the subject invention with the distal anchor wings and rotatably levered proximal anchor blades in their stowed positions.
Figure 7:
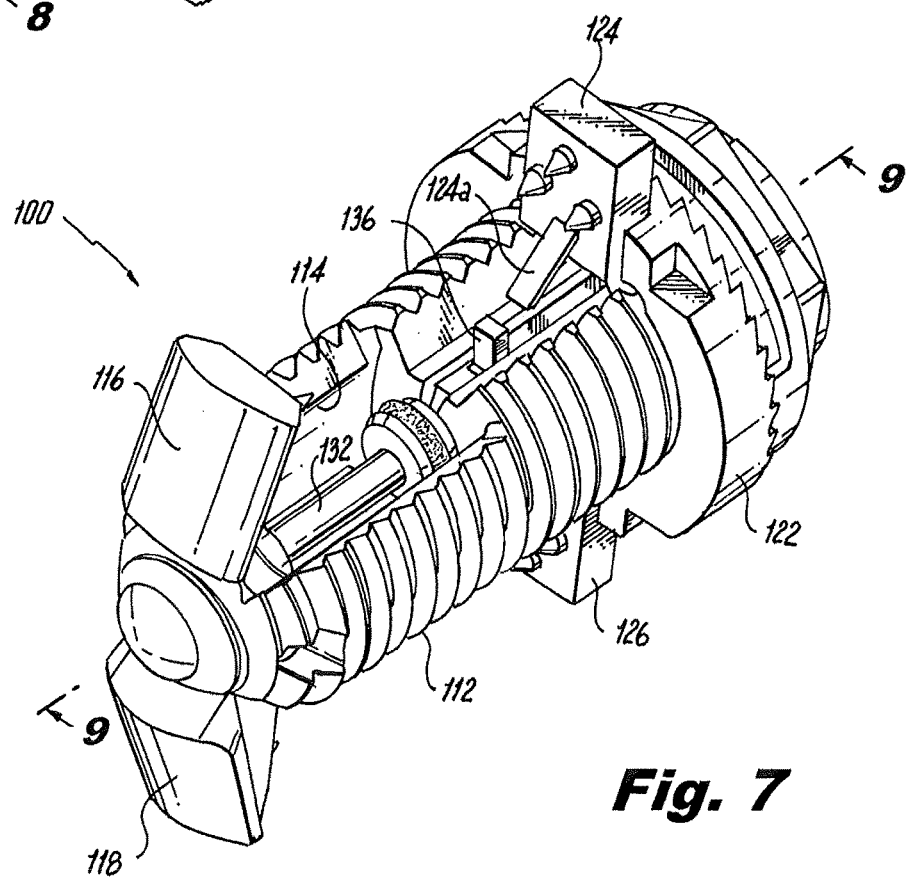
FIG. 7 is a perspective view of the interspinous process implant of FIG. 6, with the distal anchor wings and rotatably levered proximal anchor blades in their radially deployed positions.

As shown in FIG. 4, the anchor blades 24, 26 are mounted for sliding radial movement between their first and second positions, through a camming interaction with ramped surfaces 36a, 36b of the proximal actuation portion 36 of actuation shaft 32. The anchor blades 24, 26 each include a set of distal facing spikes 40 for positively engaging the spinous process during deployment. In addition, each anchor blade 24, 26 includes a pair of lateral deflectable locking tabs 42 that ride within the blade channels 28, 30 when the blades 24, 26 are advancing radially outwardly to a deployed position, but the tabs 42 expand laterally outward and engage the outer lip of the anchor collar 22 when they are fully deployed out of the blade channels 28, 30 to prevent further radially inward movement.

Referring to FIG. 3, the implant 10 further includes a locking ring 44 for securing the axial position of the anchor collar 22 with respect to the elongated body 12. The locking ring 44 has a pair of diametrically opposed, arcuate shaped, cantilevered pawls 46, 48 each with a respective set of distal facing teeth 46a, 48a for engaging a corresponding set of teeth formed on an annular rack 50 on the proximal facing surface of the anchor collar 22. The locking ring 44 has a hexagonal nut portion 52 on its proximal-most surface for manipulation using a tool (not shown).

Referring now to FIGS. 6-9, there is illustrated another interspinous process implant constructed in accordance with a preferred embodiment of the subject invention and designated generally by reference numeral 100. Implant 100 is constructed much like implant 10 described above, in that it includes pivoting distal anchor wings 116, 118; however in this embodiment the device includes anchor blades 124, 126 that are mounted for pivotal movement on the anchor collar 122, in a proximally directed angular motion, between their first position shown in FIG. 6 and their second position shown in FIG. 7.

Figure 8:
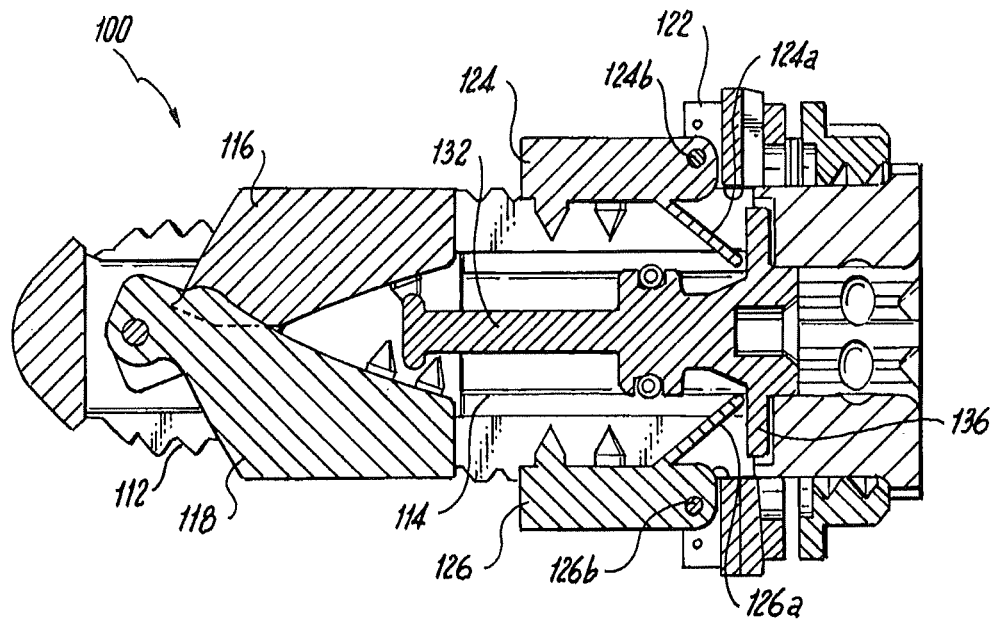
FIG. 8 is a cross-sectional view taken along line 8-8 of FIG. 6.
Figure 9:
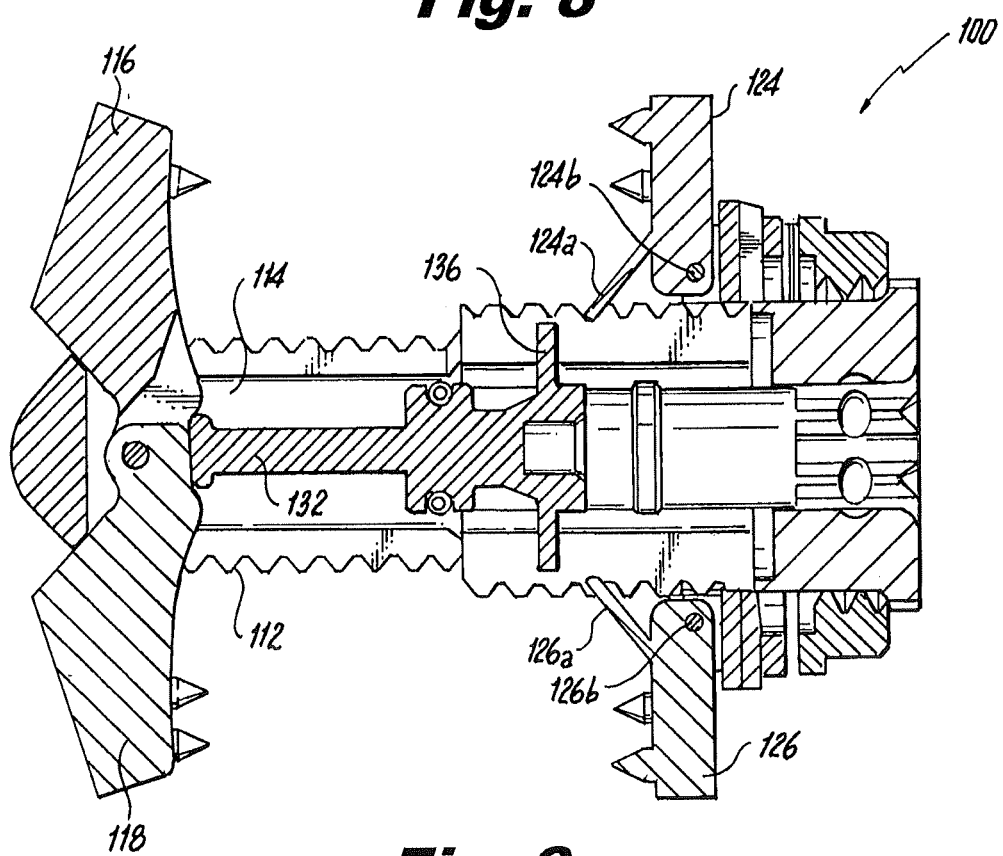
FIG. 9 is a cross-sectional view taken along line 9-9 of FIG. 7.
Figure 10:
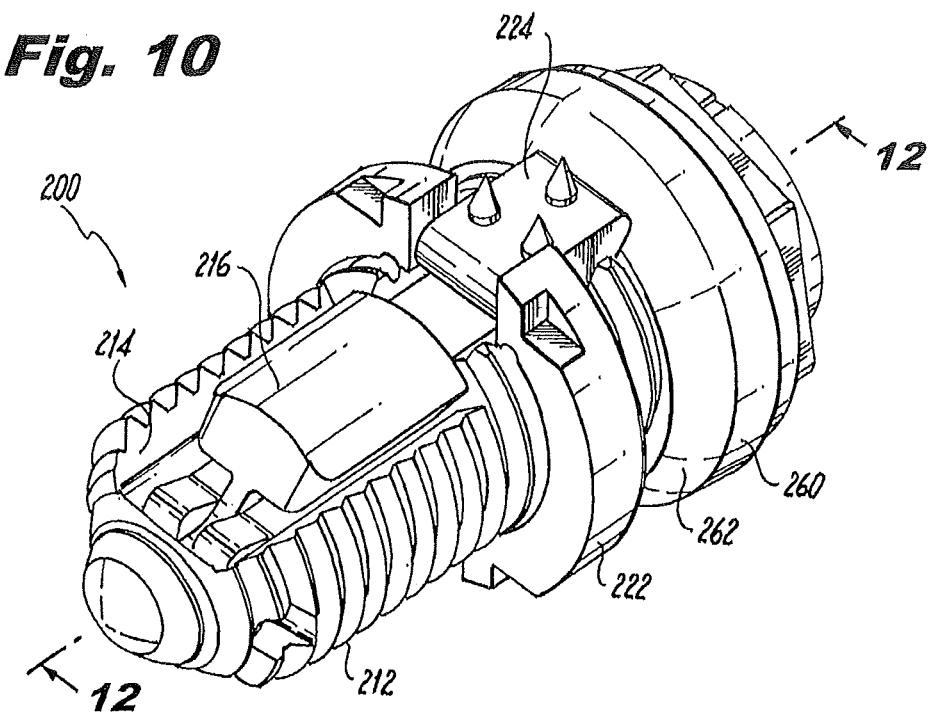
FIG. 10 is a perspective view of another interspinous process implant constructed in accordance with a preferred embodiment of the subject invention with the distal anchor wings and rotatably cammed proximal anchor blades in their stowed positions.
Figure 11:
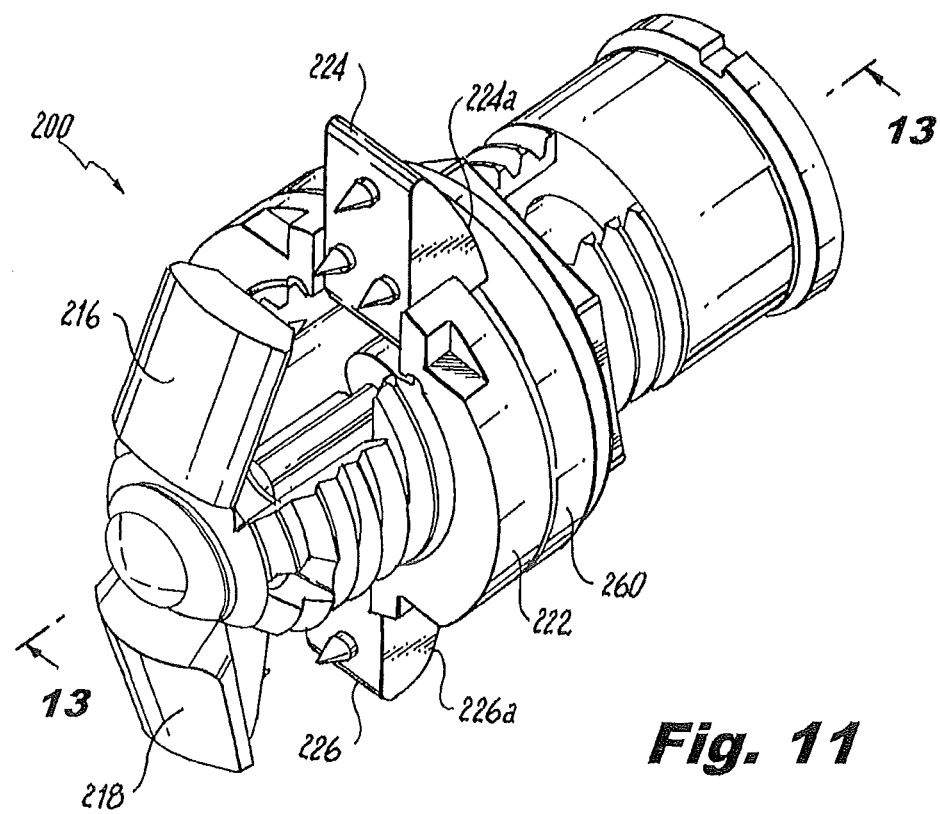
FIG. 11 is a perspective view of the interspinous process implant of FIG. 10, with the distal anchor wings and rotatably cammed proximal anchor blades in their radially deployed positions.

In addition, the anchor blades 124, 126 each include a respective interior lever 124a, 126a that is adapted and configured to interact with an annual flange 136 that forms the proximal actuation portion of an actuation shaft 132. In operation, as the annular flange 136 of actuation shaft 132 translates in a distal direction within the interior cavity 114 of body 112, it interacts with the levers 124a, 126a of anchor blades 124, 126, causing the blades 124, 126 to pivot on the anchor collar 122 about respective pivot pins 124b, 126b, from a stowed position housed partially within the interior cavity 114 of the body 112, as shown in FIG. 8, to a deployed position extending radially outwardly from the anchor collar 122, as shown in FIG. 9.

Referring now to FIGS. 10-13, there is illustrated yet another interspinous process implant constructed in accordance with a preferred embodiment of the subject invention and designated generally by reference numeral 200. Implant 200 is similar in construction to the previously described implants in that it includes pivoting distal anchor wings 216, 218; however in this embodiment the device includes anchor blades 224, 226 that are mounted for pivotal movement on the anchor collar 222, in a distally directed angular motion, between their first position shown in FIG. 10 and their second position shown in FIG. 11.

Figure 12:
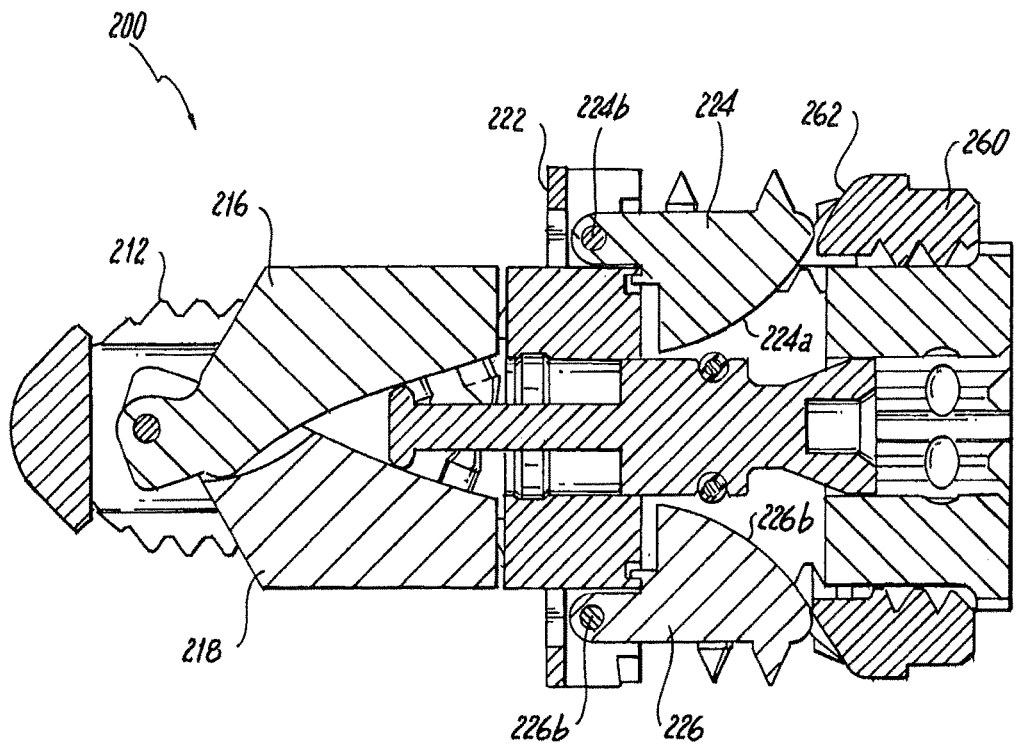
FIG. 12 is a cross-sectional view taken along line 12-12 of FIG. 10.
Figure 13:
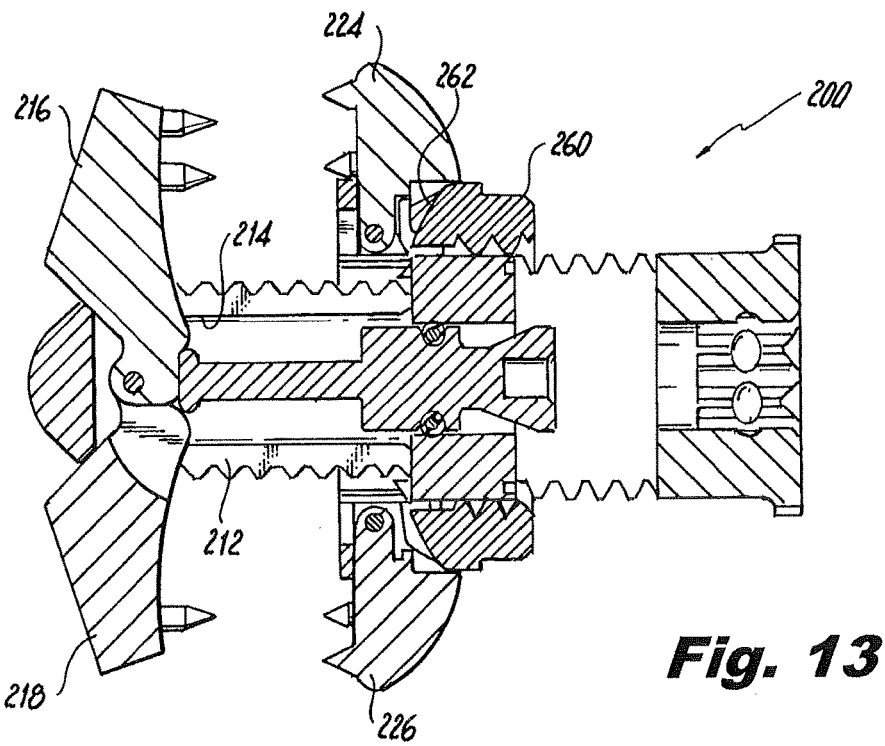
FIG. 13 is a cross-sectional view taken along line 13-13 of FIG. 11.
Figure 14:
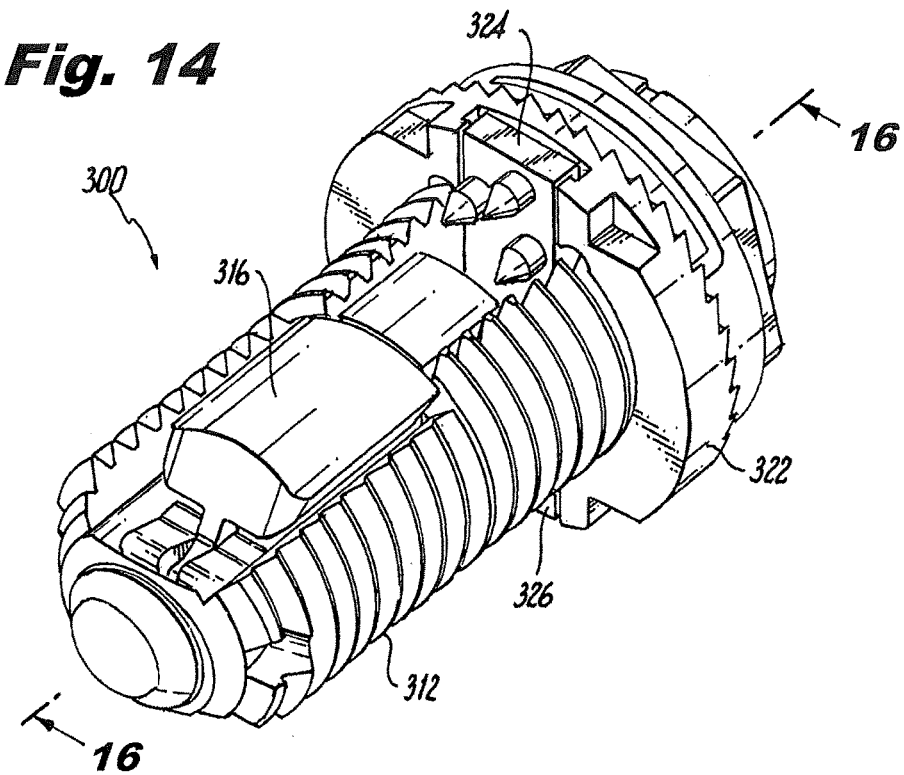
FIG. 14 is a perspective view of another interspinous process implant constructed in accordance with a preferred embodiment of the subject invention with the distal anchor wings and the slidably cammed proximal anchor blades in their stowed positions.
Figure 15:
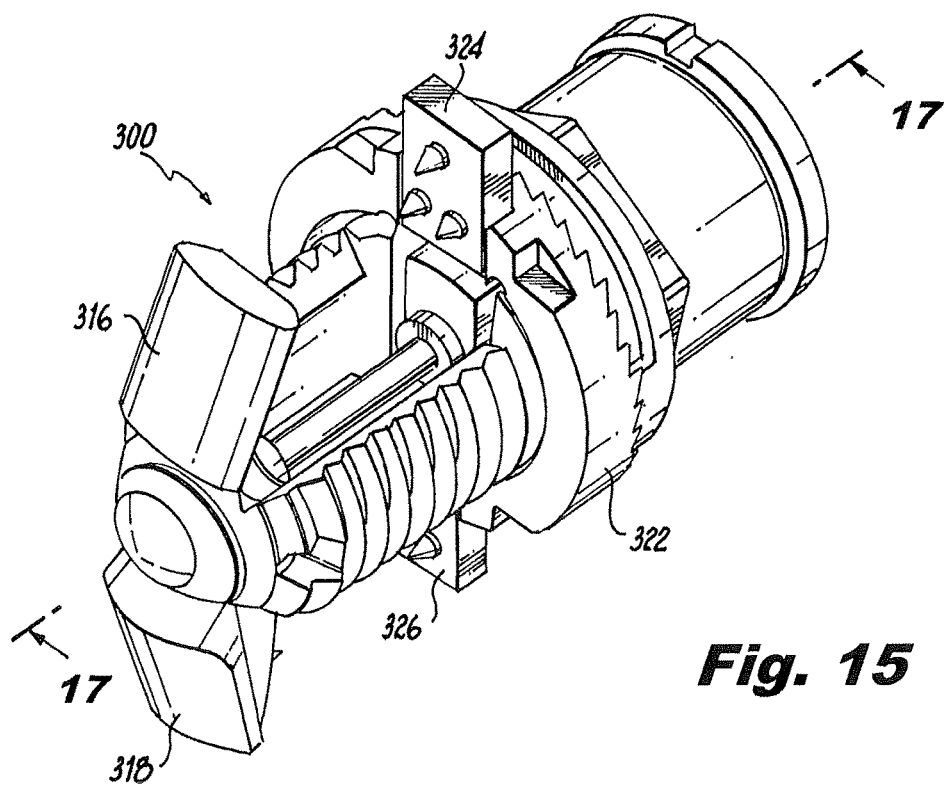
FIG. 15 is a perspective view of the interspinous process implant of FIG. 14, with the distal anchor wings and slidably cammed proximal anchor blades in their radially deployed positions.

In addition, the anchor blades 224, 226 each include a respective curved outer camming surface 224a, 226a adapted and configured to interact with a curved undersurface 262 of an annular nut 260 that is threadably associated with the body portion 212. In operation, as the annular nut 260 translates in a distal direction along body 212, it interacts with the camming surfaces 224a, 226a of anchor blades 224, 226, causing the blades 224, 226 to pivot on the anchor collar 222 about respective pivot pins 224b, 226b, from a stowed position housed partially within the interior cavity 214 of the body 212 as shown in FIG. 12, to a deployed position extending radially outwardly from the anchor collar 222 as shown in FIG. 13. Once deployed, the hinged anchor blades 224, 226 rest on the annular nut 260 to provide added strength and a locking feature.

Referring now to FIGS. 14-17, there is illustrated still another interspinous process implant constructed in accordance with a preferred embodiment of the subject invention and designated generally by reference numeral 300. Implant 300 is similar in construction to the previously described implants, in that it includes pivoting distal anchor wings 316, 318. Furthermore, in this embodiment anchor blades 324, 326 are mounted for sliding movement on the anchor collar 322, in a radially outward direction, between their first position shown in FIG. 14 and their second position shown in FIG. 15, similar to the anchor blades 24, 24 of implant 10. However, in contrast to implant 10, the anchor blades 324, 326 are adapted and configured to interact with a ramped surface 360 formed in the interior cavity 314 of the body portion 312 of implant 300.

Figure 16:
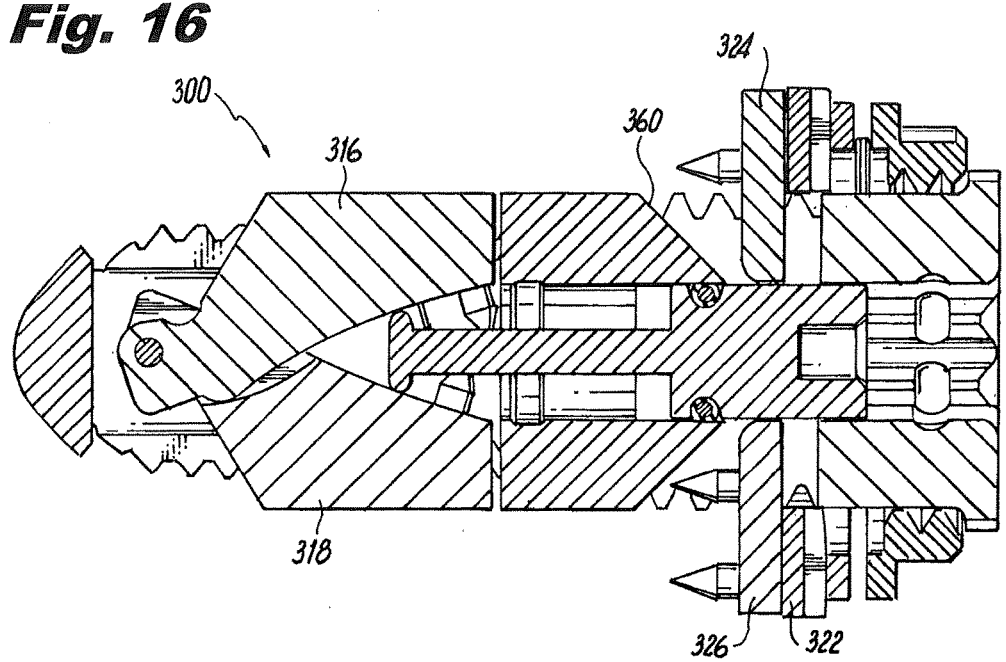
FIG. 16 is a cross-sectional view taken along line 15-15 of FIG. 14.
Figure 17:
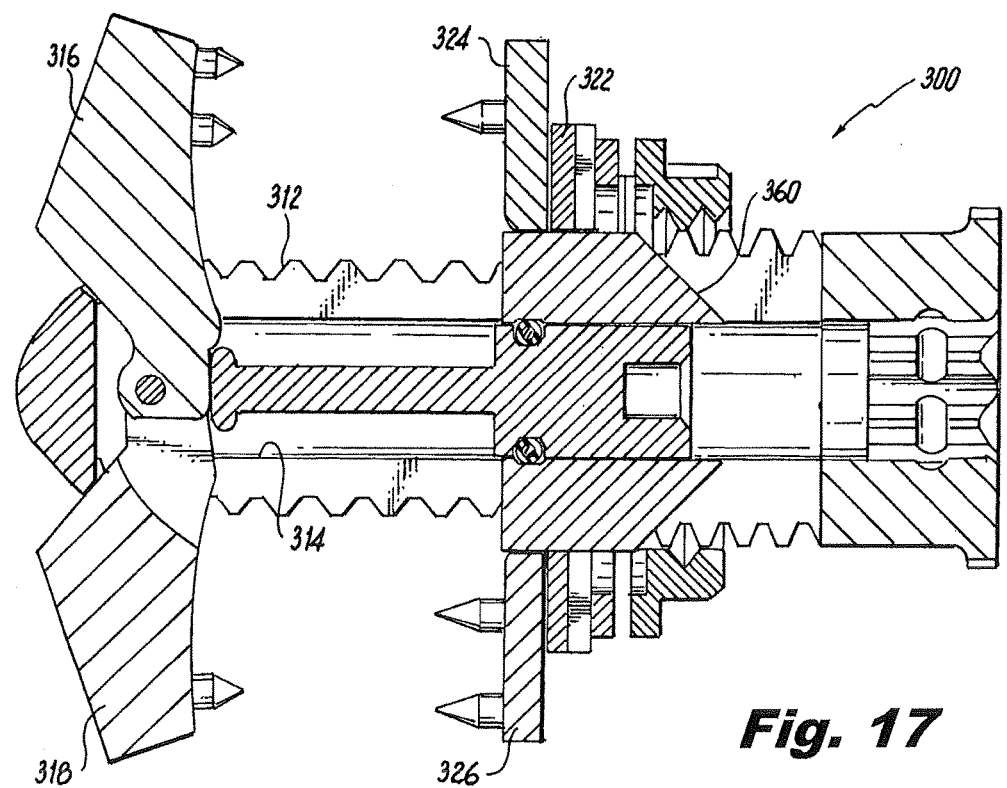
FIG. 17 is a cross-sectional view taken along line 16-16 of FIG. 15.
Figure 18:
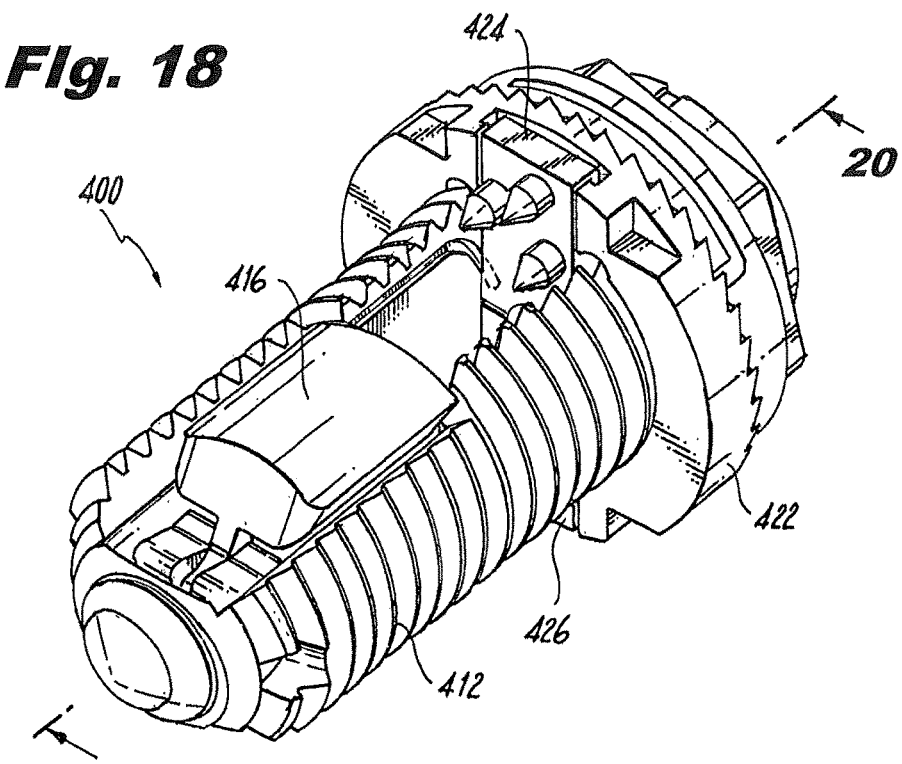
FIG. 18 is a perspective view of another interspinous process implant constructed in accordance with a preferred embodiment of the subject invention with the distal anchor wings and the track guided proximal anchor blades in their stowed positions.

In operation, as the anchor collar 322 translates in a distal direction along body 312, the interior surfaces of anchor blades 324, 326 ride along the ramped surface 360, causing the blades 324, 326 to slide radially outwardly on anchor collar 322 from a stowed position housed partially within the interior cavity 314 of the body 312 as shown in FIG. 16, to a deployed position extending radially outwardly from the anchor collar 322 as shown in FIG. 17. Once deployed, lateral locking tabs, as shown for example in FIG. 4, prevent the anchor blades 324, 326 from collapsing back into the body 312.

Referring now to FIGS. 18-22, there is illustrated another interspinous process implant constructed in accordance with a preferred embodiment of the subject invention and designated generally by reference numeral 400. Implant 400 is similar in construction to the previously described implants in that it includes pivoting distal anchor wings 416, 418; however in this embodiment the device includes anchor blades 424, 426 that are mounted to slidably translate relative to a guide track or groove 475 formed within the interior cavity 414 of body 412, on anchor collar 422, between their first position shown in FIG. 18, and their second position shown in FIG. 19.

Figure 19:
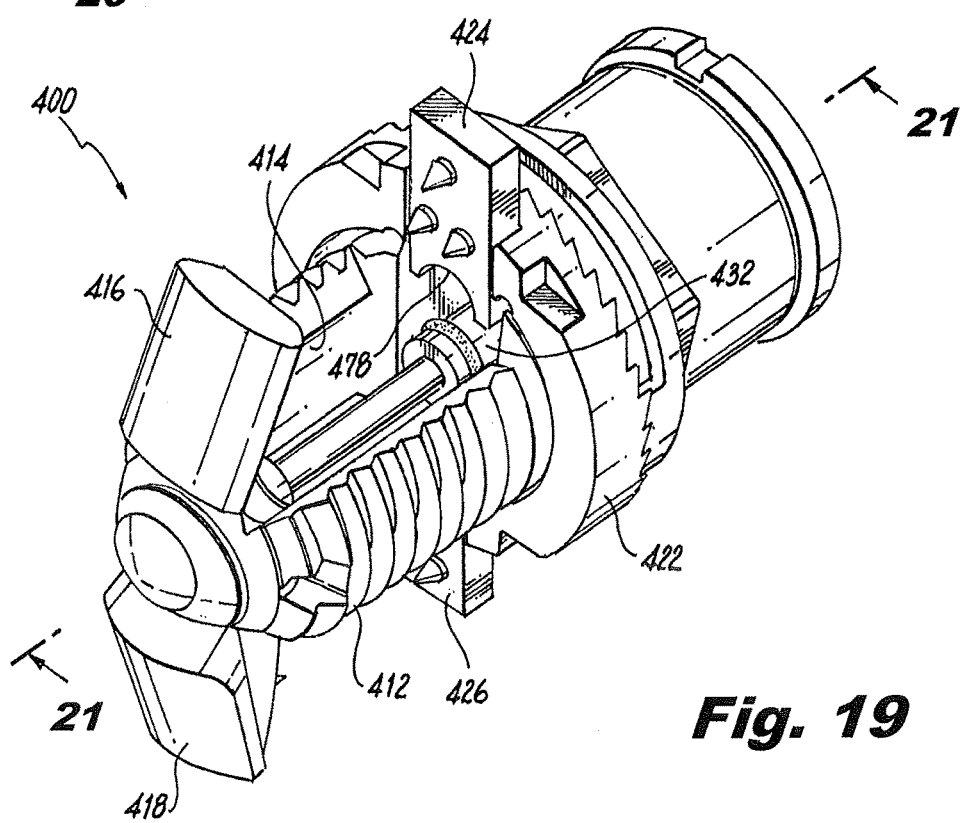
FIG. 19 is a perspective view of the interspinous process implant of FIG. 14, with the distal anchor wings and track guided proximal anchor blades in their radially deployed positions.
Figure 20:
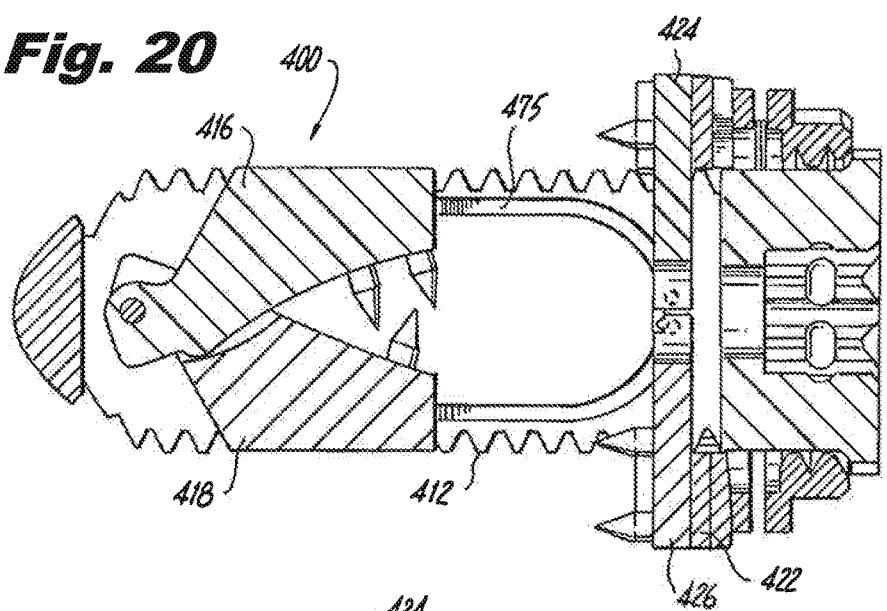
FIG. 20 is a cross-sectional view taken along line 20-20 of FIG. 18.
Figure 21:
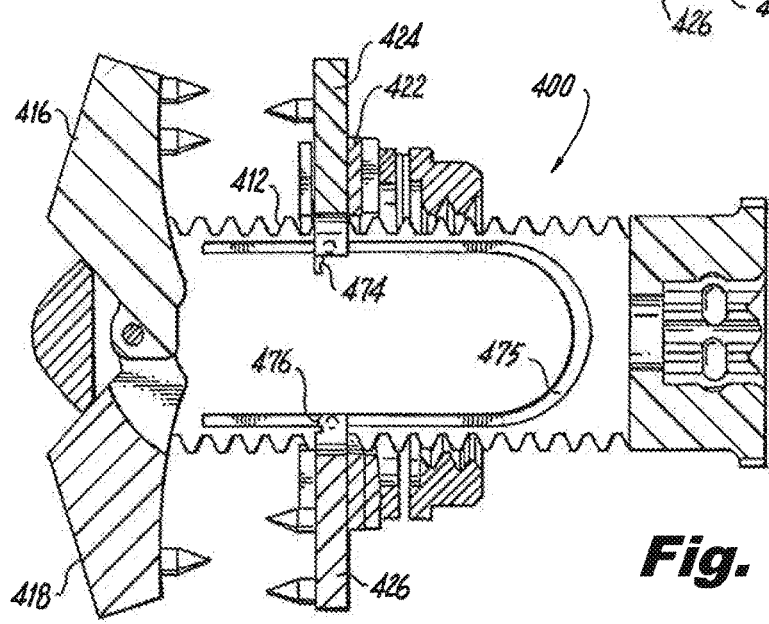
FIG. 21 is a cross-sectional view taken along line 21-21 of FIG. 19.
Figure 22:
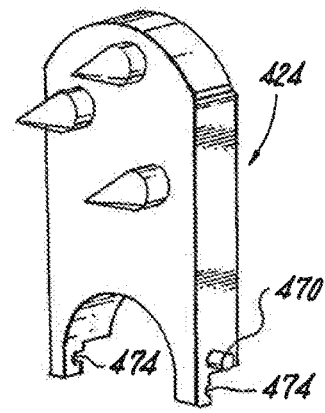
FIG. 22 is a perspective view of a track guided proximal anchor blade of the interspinous process implant of FIG. 18.
Figure 23:
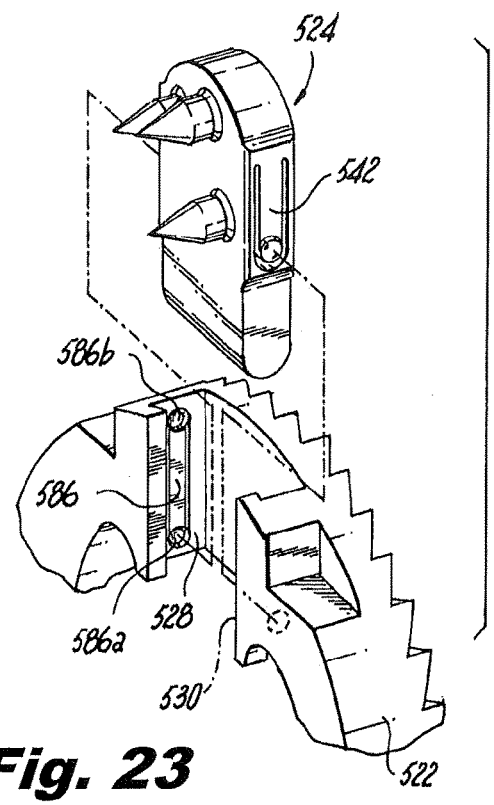
FIGS. 23-26 are views of an alternative embodiment of a locking tab structure for securing the sliding anchor blades of the subject invention in a deployed position relative to the anchor collar.
Figure 24:
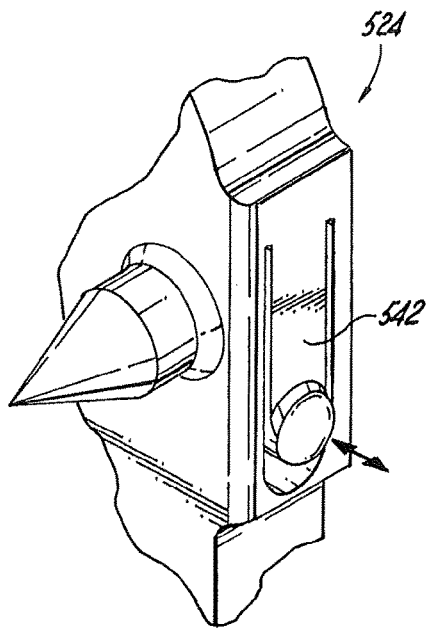
Figure 25:
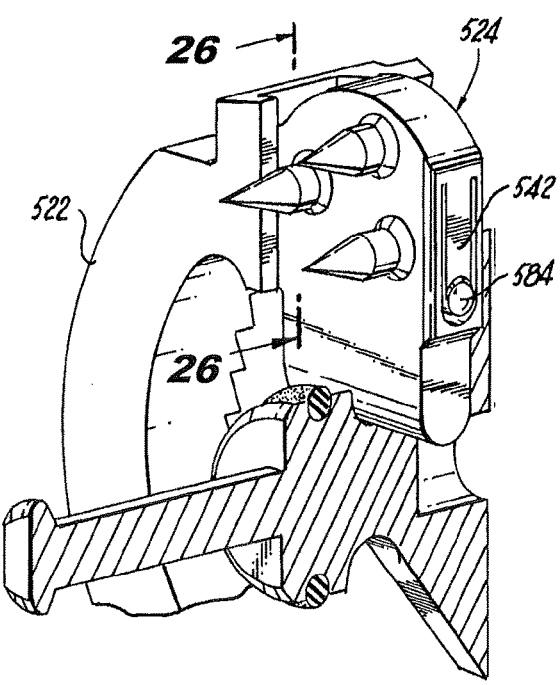
Figure 26:
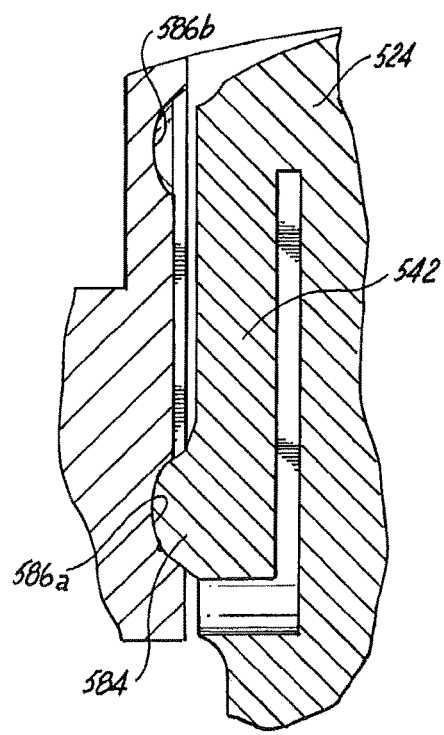

More particularly, as best seen in FIG. 22, the anchor blades 424, 426 have extension tabs 470 that ride in ramped grooves 475 cut into the interior surfaces of body 412. In operation, as the anchor collar 422 translates in a distal direction, the anchor blades 424, 426 ride along the groove 475, causing the blades 424, 426 to slide radially outwardly on anchor collar 422 from a stowed position housed partially within the interior cavity 414 of the body 412 as shown in FIG. 20, to a deployed position extending radially outwardly from the anchor collar 422 as shown in FIG. 21. Anchor blades 424, 426 have overlapping nubs 474, 476 which engage with one another when the blades are in the stowed position of FIG. 20, to prevent their premature extension. Also, a curved recess is formed in each blade to accommodate axial travel of actuation shaft 432 during deployment of the implant, as best seen in FIG. 19.

Turning now to FIGS. 23-26, there is shown an alternative embodiment of a deflectable locking tab 542 for securing a slidably deployable anchor blade 524 of the subject invention in a deployed position relative to the outer surface of an anchor collar 522. This locking tab 542 is similar to the locking tab 42 shown in FIG. 4. However, unlike locking tab 42, locking tab 542 is integrally formed in the lateral edge of the anchor blade 524, rather than separately attached thereto.

As illustrated, the deflectable locking tab 542 includes a hemispherical detent 584 that rides in a slot 586 formed in the channel walls 528, 530 of the anchor collar 522. The slot 586 includes a first recess 586a for accommodating the detent 584 when the blade is in a first position and a second recess 586b for accommodating the detent 584 when the blade is in a second position, as illustrated for example in FIG. 26.

While the subject invention has been shown and described with reference to preferred embodiments, those skilled in the art will readily appreciate that various changes and/or modifications may be made thereto without departing from the spirit and scope of the subject invention as defined by the appended claims.

What is claimed is:

1. An interspinous process implant, comprising:
   a) an elongated body dimensioned and configured for percutaneous interspinous process implantation, defining a longitudinal axis, an interior cavity and opposed proximal and distal end portions;
   b) a pair of anchor wings operatively associated with the distal end portion of the body and mounted for pivotal movement relative to the longitudinal axis of the body between a first position housed within the interior cavity of the body and a second position extending radially outwardly from the body;
   c) an anchor collar operatively associated with the proximal portion of the body and mounted for axial movement relative to the longitudinal axis of the body between a first position spaced apart from the anchor wings and a second position approximated with the anchor wings;
   d) a pair of anchor blades operatively associated with the anchor collar and mounted for radial movement within respective diametrically opposed blade channels formed in the anchor collar, between a first position housed at least partially within the interior cavity of the body and a second position extending radially outwardly from the anchor collar; and
   e) a locking ring for securing the axial position of the anchor collar with respect to the elongated body, wherein the locking ring has a pair of diametrically opposed, arcuate shaped, cantilevered pawls, each with distal facing teeth for engaging a corresponding set of teeth on the proximal facing surface of the anchor collar.

2. An interspinous process implant as recited in claim 1, further comprising an elongated actuation shaft mounted for axial movement within the interior cavity of the body and having a distal actuation portion for moving the anchor wings from their first position to their second position and a proximal actuation portion for moving the anchor blades from their first position to their second position.

3. An interspinous process implant as recited in claim 2, further comprising means for moving the actuation shaft within the interior cavity of the body.

4. An interspinous process implant as recited in claim 2, wherein each anchor blade has a cam surface for interacting with a cam on the proximal actuation portion of the actuation shaft.

5. An interspinous process implant as recited in claim 1, wherein the anchor blades are mounted for sliding movement between their first and second positions.

6. An interspinous process implant as recited in claim 5, wherein each anchor blade has a cam surface for interacting with a cam formed within the interior of the body.

7. An interspinous process implant as recited in claim 5, wherein each anchor blade includes a locking tab for securing the anchor blades in the second position relative to the anchor collar.

8. An interspinous process implant as recited in claim 1, wherein the anchor wings are diametrically opposed to one another relative to the longitudinal axis of the body and wherein the anchor blades are diametrically opposed to one another relative to the longitudinal axis of the body.

9. An interspinous process implant as recited in claim 8, wherein the diametrically opposed anchor wings are axially aligned with the diametrically opposed anchor blades.

10. An interspinous process implant as recited in claim 1, wherein the locking ring further includes a hexagonal nut portion on a proximal-most surface thereof for manipulation.

11. An interspinous process implant as recited in claim 1, wherein each anchor wing has a proximally facing engagement surface having a plurality of spikes provided thereon for engaging the spinous process.

12. An interspinous process implant as recited in claim 1, wherein each anchor blade has a distally facing engagement surface having a plurality of spikes provided thereon for engaging the spinous process.

13. An interspinous process implant, comprising:
   a) an elongated body dimensioned and configured for percutaneous interspinous process implantation, defining a longitudinal axis, an interior cavity and opposed proximal and distal end portions;
   b) a pair of diametrically opposed anchor wings operatively associated with the distal end portion of the body and mounted for pivotal movement relative to the longitudinal axis of the body between a first position housed within the interior cavity of the body and a second position extending radially outwardly from the body;
   c) an anchor collar operatively associated with the proximal portion of the body and mounted for axial movement relative to the longitudinal axis of the body between a first position spaced apart from the anchor wings and a second position approximated with the anchor wings;

d) a pair of diametrically opposed anchor blades operatively associated with the anchor collar and mounted for sliding radial movement within respective diametrically opposed blade channels formed in the anchor collar, between a first position housed within the interior cavity of the body and a second position extending radially outwardly from the anchor collar;

e) an elongated actuation shaft mounted for axial movement within the interior cavity of the body and having a distal actuation portion for pivoting the anchor wings from their first position to their second position and a proximal actuation portion for sliding the anchor blades from their first position to their second position; and f) a locking ring for securing the axial position of the anchor collar with respect to the elongated body, wherein the locking ring has a pair of diametrically opposed, arcuate shaped, cantilevered pawls, each with distal facing teeth for engaging a corresponding set of teeth on the proximal facing surface of the anchor collar.

14. An interspinous process implant as recited in claim 13, further comprising means for moving the actuation shaft within the interior cavity of the body.

15. An interspinous process implant as recited in claim 13, wherein each anchor blade has an interior cam surface for interacting with a cam on the proximal actuation portion of the actuation shaft.

16. An interspinous process implant as recited in claim 13, wherein each anchor blade includes a locking tab for securing the anchor blades in the second position relative to the anchor collar.

17. An interspinous process implant as recited in claim 13, wherein each anchor wing has a proximally facing engagement surface having a plurality of spikes provided thereon for engaging the spinous process.

18. An interspinous process implant as recited in claim 13, wherein each anchor blade has a distally facing engagement surface having a plurality of spikes provided thereon for engaging the spinous process.

19. An interspinous process implant as recited in claim 13, wherein the diametrically opposed anchor wings are axially aligned with the diametrically opposed anchor blades.

* * * * *